US00PP26019P2

(12) United States Plant Patent
Burton

(10) Patent No.: US PP26,019 P2
(45) Date of Patent: Oct. 27, 2015

(54) ***HEBE* PLANT NAMED 'JEWEL OF THE NILE'**

(50) Latin Name: ***Hebe* hybrid**
Varietal Denomination: Jewel of the Nile

(71) Applicant: Stephen Burton, Cambridge (NZ)

(72) Inventor: Stephen Burton, Cambridge (NZ)

( * ) Notice: Subject to any disclaimer, the term of this patent is extended or adjusted under 35 U.S.C. 154(b) by 23 days.

(21) Appl. No.: 13/986,359

(22) Filed: Apr. 23, 2013

Related U.S. Application Data

(60) Provisional application No. 61/687,958, filed on May 3, 2012.

(51) Int. Cl.
*A01H 5/00* (2006.01)

(52) U.S. Cl.
USPC ..... Plt./226

(58) Field of Classification Search
USPC ..... Plt./263.1, 226
See application file for complete search history.

(56) References Cited

PUBLICATIONS

Tui Garden 2011.*
UPOV 'Record Detail' , 2014.*

* cited by examiner

*Primary Examiner* — Keith O. Robinson
(74) *Attorney, Agent, or Firm* — Penny J. Aguirre

(57) ABSTRACT

A new cultivar of *Hebe*, 'Jewel of the Nile', characterized by its variegated leaves with olive green centers and yellow margins that are tinged with purple, its long narrow leaves with midribs on the upper and lower surface purple in color, its young leaves that are tinged with mauve purple at the leaf base, its purple stems, its that are resistant to leaf spot, and its mauve pink flowers.

2 Drawing Sheets

Botanical classification: *Hebe* hybrid.
Cultivar designation: 'Jewel of the Nile'.

BACKGROUND OF THE INVENTION

The present invention relates to a new and distinct cultivar of *Hebe*, botanically of hybrid origin and in the group Comm. ex Juss. and known as *Hebe* 'Jewel of the Nile' and will be referred to hereafter by its cultivar name, 'Jewel of the Nile'. 'Jewel of the Nile' is grown for use as a container plant and as a landscape shrub.

The new cultivar was discovered as a unique seedling in the Inventor's nursery in summer of 2010 in Cambridge, New Zealand. The new cultivar resulted from open pollination of an unnamed and unpatented *Hebe* plant in the Inventors breeding program in a trial plot planted with a collection of *Hebe* grown from seed. The male parent is therefore unknown.

Asexual reproduction of the new cultivar was first accomplished by the Inventor using terminal stem cuttings in Cambridge, New Zealand in 2010. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Jewel of the Nile' as a new and distinct cultivar of *Hebe*.

1. 'Jewel of the Nile' exhibits variegated leaves with olive green centers and yellow margins that are tinged with purple.
2. 'Jewel of the Nile' exhibits long narrow leaves.

3. 'Jewel of the Nile' exhibits leaves with the midrib on the upper and lower surface purple in color.
4. 'Jewel of the Nile' exhibits young leaves that are tinged with mauve purple at the leaf base.
5. 'Jewel of the Nile' exhibits stems that are purple in color.
6. 'Jewel of the Nile' exhibits leaves that are resistant to leaf spot.
7. 'Jewel of the Nile' exhibits mauve pink flowers.

'Jewel of the Nile' differs from its seed plant in having brighter and clearer leaf colors, more distinct purple coloration on the stems and leaf veins, more distinct yellow margins, and increases resistance to leaf spot. 'Jewel of the Nile' can be most closely compared to the cultivars 'Grace Kelly' (U.S. Plant Pat. No. 22,653) and 'Orphan Annie' (not patented). 'Grace Kelly' differs from 'Jewel of the Nile' in having variegated foliage that has lighter yellow margins, in having less purple coloration on the stems, leaf base, and leaf veins, in having less elongated leaves, and in having darker colored flowers. 'Orphan Annie' differs from 'Jewel of the Nile' in having new leaf tips that are tinged with magenta rather than yellow, and in having less intense purple coloration on the stems, leaf base, and leaf veins.

BRIEF DESCRIPTION OF THE DRAWING

The accompanying colored photographs illustrate the overall appearance and distinct characteristics of the new *Hebe*. The photographs were taken of a plant approximately one year in age as grown in an 18-cm container outdoors in Cambridge, New Zealand.

The photograph in FIG. 1 is a top view of 'Jewel of the Nile' just beginning to bloom.

Figure 1:
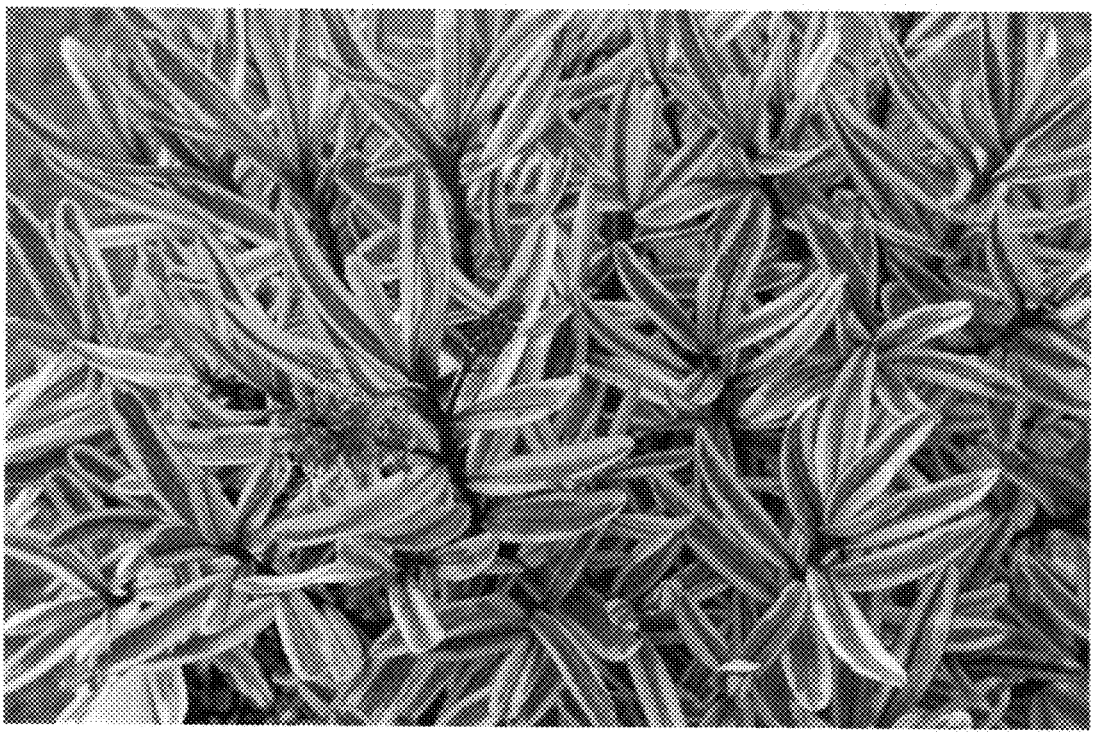
Figure 2:
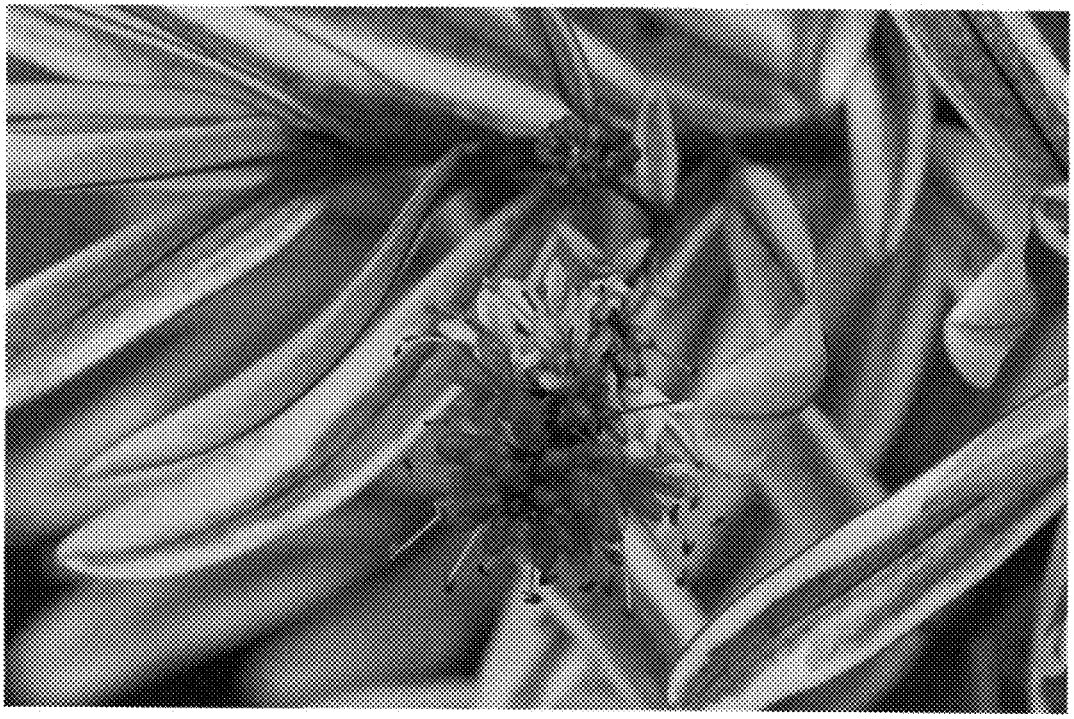

The photograph in FIG. 2 provides a close-up view of the inflorescences and leaves of 'Jewel of the Nile'.

The colors in the photographs may differ slightly from the color values cited in the detailed botanical description, which accurately describe the colors of the new *Hebe*.

DETAILED BOTANICAL DESCRIPTION OF THE PLANT

The following is a detailed description of one year-old plants of the new cultivar as grown outdoors in 18-cm containers in Cambridge, New Zealand. Plants were grown under average day temperatures of 20° to 28° C. and average night temperatures of 12° to 16° C. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General plant characteristics:

*Plant type*.—Perennial shrub.

*Plant habit*.—Rounded, upright and spreading.

*Flowering period*.—12 weeks late summer in New Zealand.

*Height and spread*.—Reaches 50 to 70 cm in height and about 70 cm in width.

*Hardiness*.—U.S.D.A. Zones 9b, 10a, and 10b.

*Disease resistance*.—Resistant to leaf spot caused by *Kirramyces hexes*.

*Root description*.—Fibrous and fine, 1 to 3 mm in diameter, 176D in color.

Growth and propagation:

*Growth rate*.—Moderate.

*Propagation type*.—Terminal stem cuttings.

*Root initiation*.—About 14 to 18 days at 20° C. under mist in a greenhouse and ambient light.

*Root development*.—8 weeks from rooted cutting to liner transfer and about 12 weeks to fully develop a liner with one trim.

Stem description:

*Stem size*.—Lateral branches are an average of 25 to 45 cm in length and 4 to 6 mm in width.

*Stem shape*.—Round.

*Stem color*.—N77B.

*Stem surface*.—Smooth.

*Stem strength*.—Brittle.

*Internode length*.—Average of 8 mm.

*Branching habit*.—Freely branched from base, average of 10 lateral branches.

Foliage description:

*Leaf shape*.—Elongated oblong.

*Leaf division*.—Single.

*Leaf base*.—Canoe shaped, obtuse.

*Leaf apex*.—Canoe shaped, obtuse.

*Leaf venation*.—Only mid rib is visible, color: upper surface; N77B, lower surface 77A.

*Leaf margins*.—Smooth entire.

*Leaf attachment*.—Sessile.

*Leaf arrangement*.—Opposite simple sessile.

*Leaf surface*.—Glabrous and semi-glossy on upper and lower leaf surface.

*Leaf color*.—Upper young surface; 12B, margins 11C and center 194B and base N77B, mature upper surface; 11B, margins 11D and center 191C and base N77B, lower young surface; 194B, margin 196B and vein and base 77A, mature lower surface; 195B, margin 11B and vein and base 77A.

*Leaf number*.—Average of 20 to 30 per lateral branch.

*Leaf size*.—6 to 9 cm in length and 1 to 1.5 cm in width.

*Leaf aspect*.—Held nearly horizontal to slightly upright to stem.

*Leaf density*.—Dense.

*Leaf fragrance*.—None.

Flower description:

*Inflorescence type*.—Multiple florets on a raceme.

*Inflorescence size*.—4 to 5 cm in length and 1.5 to 2 cm in width.

*Inflorescence lastingness*.—About 4 to 6 weeks, persistant.

*Flower shape*.—Raceme is tapered with trumpet shaped florets.

*Flower fragrance*.—None.

*Flower quantity*.—Average of 50 to 60 florets per inflorescence.

*Flower density*.—Densely arranged in inflorescence.

*Flower arrangement*.—Paired racemes on extended peduncle from the leaf axis, 2 to 4 racemes per lateral stem.

*Flower aspect*.—Slightly drooping racemes.

*Flower size*.—Average of 7 mm in depth and 5 mm in diameter.

*Peduncles*.—Weak in strength, 1 to 2 cm in length and about 1 mm in width, N77B in color, surface is sparsely covered in short hairs, round in shape, held at about a 30° angle to stem.

*Pedicels*.—Average of 2 mm in length and >1 mm in width, held at about a 50° to 60° angle to peduncle, N77B in color, surface is smooth.

*Flower buds*.—Oblong in shape and slightly pointed at the tip, 1 to 2 mm in length and 0.5 to 1 mm in diameter, 59C in color.

*Calyx*.—Cup-shaped, average of 1 mm in length and 1.5 mm in diameter.

*Sepals*.—3, very small and lanceolate in shape, apex is pointed, base tapers to pedicel, color of young upper and lower surface when opening; 59C, color of mature upper and lower surface; 59D, average of 1 mm in length and 0.5 mm in width.

*Corolla*.—3 to 4 petals form a ring to comprise trumpet shape, 4 mm in width.

*Petals*.—From 3 to 4, about 2 to 3 mm in length and 1 to 2 mm in width, smooth margins, apex rounded, upper and lower surface is glabrous, color of upper and lower surface when opening; 61B, color of upper surface when fully open; 60C, color of lower surface when fully open; 61D with fused base, color of both surfaces after fading; 61D.

Reproductive organs:

*Gynoecium*.—1 Pistil, 8 to 9 mm in length, stigma is slightly rounded in shape and N77B in color, style is about 5 to 6 mm in length and N77B in color, ovary is N77C in color.

*Androcoecium*.—2 stamens, anthers are heart shaped and 200A in color, filaments are about 9 mm in length and 186C in color, pollen is moderate in quantity and 18B in color.

*Fruit and seed*.—Viable seeds are not produced.

It is claimed:

1. A new and distinct cultivar of *Hebe* plant named 'Jewel of the Nile' as herein illustrated and described.

* * * * *